(12) United States Patent
Ignatyev et al.

(10) Patent No.: US 7,999,111 B2
(45) Date of Patent: Aug. 16, 2011

(54) PROCESS FOR THE PREPARATION OF ONIUM ALKYLSULFONATES

(75) Inventors: Nikolai (Mykola) Ignatyev, Duisburg (DE); Urs Welz-Biermann, Heppenheim (DE); Andriy Kucheryna, Kyiv (UA); Helge Willner, Muehlheim/Ruhr (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 176 days.

(21) Appl. No.: 11/995,460

(22) PCT Filed: Jun. 14, 2006

(86) PCT No.: PCT/EP2006/005741
§ 371 (c)(1),
(2), (4) Date: Jan. 11, 2008

(87) PCT Pub. No.: WO2007/006387
PCT Pub. Date: Jan. 18, 2007

(65) Prior Publication Data
US 2008/0221334 A1    Sep. 11, 2008

(30) Foreign Application Priority Data
Jul. 14, 2005    (DE) .......................... 10 2005 032 836

(51) Int. Cl.
C07D 211/10    (2006.01)
C07D 233/58    (2006.01)
C07D 207/06    (2006.01)
C07C 211/63    (2006.01)
C07C 321/14    (2006.01)
C07F 9/54      (2006.01)

(52) U.S. Cl. ..................... 546/347; 548/335.1; 548/579; 564/291; 564/500; 568/11

(58) Field of Classification Search .................. 549/400; 546/332, 347; 514/357; 548/335.1, 579; 564/291, 500; 568/11
See application file for complete search history.

(56) References Cited

U.S. PATENT DOCUMENTS

| | | | |
|---|---|---|---|
| 3,637,622 | A | 1/1972 | Monaco et al. |
| 7,501,522 | B2 | 3/2009 | Maase et al. |
| 2005/0070717 | A1 | 3/2005 | Wasserscheid et al. |
| 2006/0149074 | A1 | 7/2006 | Maase et al. |
| 2007/0255064 | A1 | 11/2007 | Szarvas et al. |
| 2008/0009633 | A1 | 1/2008 | Szarvas et al. |
| 2008/0033209 | A1 | 2/2008 | Szarvas et al. |
| 2008/0227987 | A1* | 9/2008 | Ignatyev et al. ........... 548/335.1 |

FOREIGN PATENT DOCUMENTS

| | | |
|---|---|---|
| WO | WO-96/18459 | 6/1996 |
| WO | WO-02/30878 | 4/2002 |
| WO | WO-02/34722 | 5/2002 |
| WO | WO 03051894 A1 * | 6/2003 |
| WO | WO-03074494 | 9/2003 |
| WO | WO 2004080974 A1 | 9/2004 |
| WO | WO 2005019183 A1 | 3/2005 |
| WO | WO-2006 021302 | 3/2006 |
| WO | WO-2006 021303 | 3/2006 |
| WO | WO-2006 021304 | 3/2006 |

OTHER PUBLICATIONS

"Ionic Liquids in Synthesis", by Wassercheid and Tom Welton (Eds), Wiley-VCH Verlag, 2003, Chapter 2, pp. 7-40.*
L. Brinchi et al, "Ionic liquids as reaction media for esterification of carboxylate sodium salts with alkyl halides", Tetrahedron letters, vol. 44 No. 10, Mar. 3, 2003, pp. 2027-2029, XP004410058, Elsevier Science, Oxford, GB.
J. Golding et al, "Methanesulphonate and p-toluenesulphonate salts of the N-methyl-N-alkylpyrrolidinium and quaternary ammonium cations: novel low cost ionic liquids", Green Chemistry, vol. 4 No. 3, 2002, pp. 223-229, XP009042135, Royal Society of Chemistry, Letchworth, GB.
J. L Kaar et al, "Impact of ionic liquid physical properties on lipase activity and stability", Journal of Organic Chemistry, vol. 125 No. 14, Mar. 13, 2003, pp. 4125-4131, XP002395793, American Chemical Society, Washington, DC USA.
W. Voss et al, "Uber die ester der schwefligen Saure. I", Justus Liebigs Annalen Der Chemie, vol. 485, 1931, pp. 258-283, XP000913973, Verlag Chemie, Weinheim, DE.
Brook, A. et al., "The mechanism of the isomerisation of dimethyl suphite to merthyl methanesulphonate," Journal Chem. Soc., 1971, pp. 1160-1162.
Mallion, K. et al., "The conditions determining the quaternisation of tertiary phosphines by methyl 2,4-dinitrosulphonate," J. Chem. Soc., 1964, pp. 5716-5725; XP009073419.
Databse WPI Week 1988 Derwent Publications Ltd., London, GB; AN 19880356115 SP002401878 & JP63 262830a (Mitsubishi Petrochemical Co Ltd) Oct. 31, 1988.
Databse WPI Week 2002 Derwent Publications Ltd., London, GB; AN 2002-419496 XP002402094 & JP 2001 322970 (Tonen Kagaku KK) Nov. 20, 2001.
Definition of Dimethyl sulfite from Wikipedia dated Nov. 3, 2010.
Definition of Methyl methanesulfonate from Wikipedia dated Nov. 3, 2010.

* cited by examiner

*Primary Examiner* — Joseph Kosack
(74) *Attorney, Agent, or Firm* — Millen, White, Zelano & Branigan, P.C.

(57) ABSTRACT

The invention relates to a process for the preparation of onium alkylsulfonates by reaction of an onium halide or carboxylate with a symmetrically substituted dialkyl sulfite or with an asymmetrically substituted dialkyl sulfite at temperatures of 50 to 170° C.

14 Claims, No Drawings

PROCESS FOR THE PREPARATION OF ONIUM ALKYLSULFONATES

The invention relates to a process for the preparation of onium alkylsulfonates by reaction of an onium halide or carboxylate with a symmetrically substituted dialkyl sulfite or with an asymmetrically substituted dialkyl sulfite at temperatures of 50 to 170° C., and to alkylsulfonates prepared by this process.

A large number of onium salts, for example alkylsulfonates, are ionic liquids. Due to their properties, ionic liquids represent an effective alternative to traditional volatile organic solvents for organic synthesis in modern research. The use of ionic liquids as novel reaction medium could furthermore be a practical solution both to solvents emission and also to problems in the reprocessing of catalysts.

Ionic liquids or liquid salts are ionic species which consists of an organic cation and a generally inorganic anion. They do not contain any neutral molecules and usually have melting points below 373 K. However, the melting point may also be higher without limiting the utility of the salts in all areas of application. Examples of organic cations are, inter alia, tetraalkylammonium, tetraalkylphosphonium, N-alkylpyridinium, 1,3-dialkylimidazolium or trialkylsulfonium. Amongst a multiplicity of suitable anions, mention may be made, for example, of $BF_4^-$, $PF_6^-$, $SbF_6^-$, $NO_3^-$, $CF_3SO_3^-$, $(CF_3SO_2)_2N^-$, $arylSO_3^-$, $CF_3CO_2^-$, $CH_3CO_2^-$ or $Al_2Cl_7^-$.

A general method for the preparation of onium alkylsulfonates is alkylation of an organic base, for example an amine, phosphine, guanidine or a heterocyclic base, using alkyl esters of alkanesulfonic acids, also known from publication in the book "Ionic Liquids in Synthesis" by P. Wasser-scheid and Tom Welton (Eds.), WILEY-VCH Verlag, 2003. In this method, the alkyl group is transferred from the ester group to the organic base with formation of the corresponding salt. The above-mentioned method has the disadvantage that the methyl esters of alkanesulfonic acids are generally toxic and may remain in the ionic liquid as impurities. In addition, access to corresponding esters is limited, i.e. only a few representatives of this class of substances are available in sufficient quantity, and in addition they are also relatively expensive. A further disadvantage of this method is that a substituent of the onium alkylsulfonate forming always corresponds to the corresponding alkyl group of the alkanesulfonic acid alkyl ester employed. The preparation of onium alkylsulfonates containing freely selectable alkyl groups in the cation is thus restricted since the alkyl radical is always transferred from the ester group to the cation. This further restricts the possibilities of the synthesis of ionic liquids of this type.

WO 2003/074494 describes ionic liquids based on sulfates and sulfonates, but does not mention a process for the preparation of corresponding sulfonates.

The object of the present invention was accordingly to provide an alternative process for the preparation of onium alkylsulfonates which results in alkylsulfonates having a freely selectable substitution pattern in the cation and anion.

The object is achieved by the process according to the invention. The invention therefore relates to a process for the preparation of onium alkylsulfonates by reaction of an onium halide or onium carboxylate with a symmetrically substituted dialkyl sulfite or with an asymmetrically substituted dialkyl sulfite at temperatures of 50 to 170° C. Surprisingly, it has been found that in this reaction, not only does exchange of the halide or carboxylate anion take place, but isomerisation of the sulfite unit to give a sulfonate unit also takes place due to the influence of the halide or carboxylate. The process according to the invention has the advantage that an alkyl group is not transferred from the sulfite employed to the cation, and the substitution pattern in the cation is thus independent of the choice of alkanesulfonate anion. In addition, the dialkyl sulfites employed are less toxic than the alkylsulfate esters. The by-products obtained in the process according to the invention are alkyl halides or esters, which can themselves be employed as valuable reagents. The alkyl halides forming as by-product on use of onium halides are, in addition, generally gases or readily volatile compounds, which can be removed from the reaction mixture without major processengineering effort.

It is of course possible to use both symmetrically substituted dialkyl sulfites having 1 to 10 C atoms or to use asymmetrically substituted dialkyl sulfites having 1 to 10 C atoms or even more highly alkylated starting materials in the process according to the invention.

Onium halides which are suitable for the process according to the invention are ammonium halides, phosphonium halides, thiouronium halides, guanidinium halides or halides with a heterocyclic cation, where the halides can be selected from the group chlorides, bromides or iodides. Phosphonium, thiouronium, guanidinium halides or halides with a heterocyclic cation are preferably employed in the process according to the invention. Besides the above-mentioned cations, uronium iodides are, in addition, also suitable.

Onium carboxylates which are suitable for the process according to the invention are ammonium carboxylates, phosphonium carboxylates, thiouronium carboxylates, guanidinium carboxylates or carboxylates with a heterocyclic cation, where the carboxylates can be selected from the group of the carbonates, formates, acetates, propylates or butylates. Ammonium, phosphonium, guanidinium carboxylates or carboxylates with a heterocyclic cation are preferably employed in the process according to the invention, in particular ammonium, phosphonium, guanidinium acetates or acetates with a heterocyclic cation.

Onium halides are preferably employed in the processes according to the invention.

The onium halides or carboxylates are generally commercially available or can be prepared by synthetic methods as are known from the literature, for example in the standard works, such as Houben-Weyl, Methoden der organischen Chemie [Methods of Organic Chemistry], Georg-Thieme-Verlag, Stuttgart, or Richard C. Larock, Comprehensive Organic Transformations, 2nd Edition, Wiley-VCH, New York, 1999. Use may also be made here of variants known per se which are not mentioned here in greater detail.

Ammonium or phosphonium halides can be described, for example, by the formula (1)

$$[XR_4]^+Hal^- \qquad (1),$$

where
X denotes N, P
Hal denotes Cl, Br or I and
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms,
where one or more R may be partially substituted by Cl, Br and/or CN or partially or fully by F, or F and Cl, or F and Br, or F, Cl and Br, but where all four or three R cannot be fully substituted by halogens,
and where one or two non-adjacent carbon atoms of the R which are not in the α- or ω-position may be replaced by atoms and/or atom groups selected from the group —O—, —C(O)—, —S—, —S(O)— or —SO$_2$.

Accordingly, compounds of the formula (1) in which all four or three substituents R are fully substituted by halogens, for example tris(trifluoromethyl)methylammonium chloride, tetra(trifluoromethyl)ammonium chloride or tetra(nonafluorobutyl)phosphonium chloride, are excluded.

Guanidinium halides can be described, for example, by the formula (2)

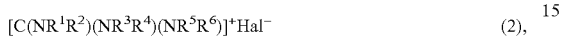
[C(NR$^1$R$^2$)(NR$^3$R$^4$)(NR$^5$R$^6$)]$^+$Hal$^-$     (2), where
Hal denotes Cl, Br or I and
R$^1$ to R$^6$ each, independently of one another, denote hydrogen or CN,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents R$^1$ to R$^6$ may be partially substituted by NO$_2$, CN, Cl and/or Br, partially or fully by F, or F and Cl, or F and Br or F, Cl and Br, but where all substituents on an N atom cannot be fully substituted by halogens,
where the substituents R$^1$ to R$^6$ may be connected to one another in pairs by a single or double bond and
where, in the substituents R$^1$ to R$^6$, one or two non-adjacent carbon atoms which are not bonded directly to the heteroatom and are not in the ω-position may be replaced by atoms and/or atom groups selected from the group —O—, —C(O)—, —S—, —S(O)— or —SO$_2$—.

Uronium and thiouronium halides can be described, for example, by the formula (3)

[(R$^1$R$^2$N)—C(=YR$^7$)(NR$^3$R$^4$)]$^+$Hal$^-$     (3), where
Y denotes O, S
Hal denotes Br or I, with the proviso that, in the case where Y=O, Hal=I, and
R$^1$ to R$^4$ and R$^7$ each, independently of one another, denote hydrogen or CN, where hydrogen is excluded for R$^7$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents R$^1$ to R$^4$ and R$^7$ may be partially or fully substituted by F, Cl and/or Br, in particular —F and/or —Cl, or partially by CN, but where all substituents on an N atom cannot be fully substituted by halogens,
where the substituents R$^1$ to R$^4$ and R$^7$ may be connected to one another in pairs by a single or double bond and where, in the substituents R$^1$ to R$^4$ and R$^7$, one or two non-adjacent carbon atoms which are not bonded directly to the heteroatom and are not in the ω-position may be replaced by atoms and/or atom groups selected from the group —O—, —C(O)—, —S—, —S(O)— or —SO$_2$—.

Halides with a heterocyclic cation can be described, for example, by the formula (4)

[HetN]$^+$Hal$^-$     (4), where
Hal denotes Cl, Br or I and
HetN$^+$ denotes a heterocyclic cation selected from the group

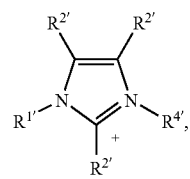
imidazolium

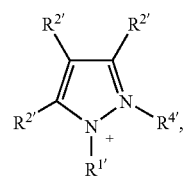
1H-pyrazolium

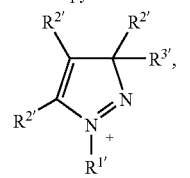
3H-pyrazolium

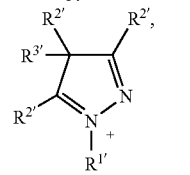
4H-pyrazolium

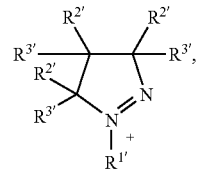
1-pyrazolinium

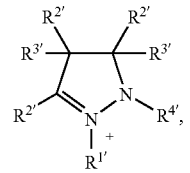
2-pyrazolinium

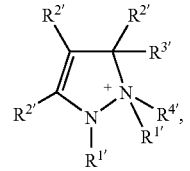
3-pyrazolinium

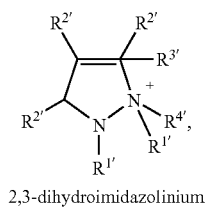
2,3-dihydroimidazolinium
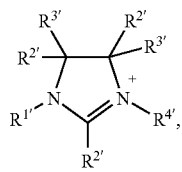
4,5-dihydroimidazolinium
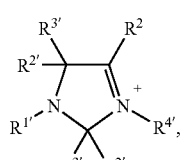
2,5-dihydroimidazolinium
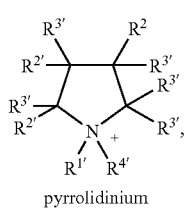
pyrrolidinium
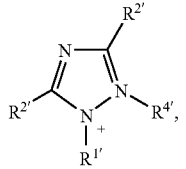
1,2,4-triazolium
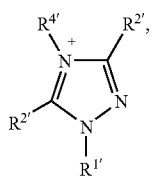
1,2,4-triazolium
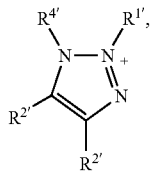
1,2,3-triazolium
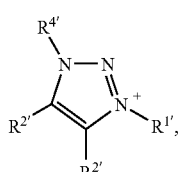
1,2,3-triazolium
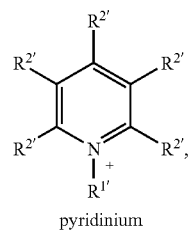
pyridinium
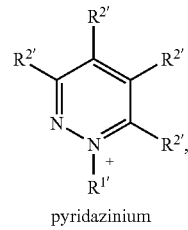
pyridazinium
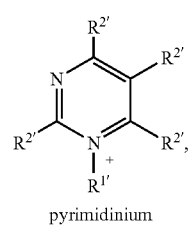
pyrimidinium
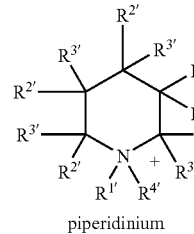
piperidinium
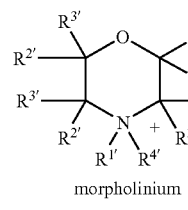
morpholinium
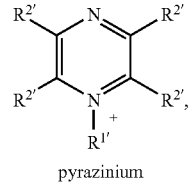
pyrazinium
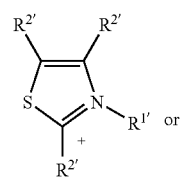
thiazolium

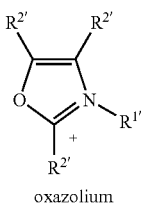

oxazolium where the substituents
R[1'] to R[4'] each, independently of one another, denote
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms,
or aryl-$C_1$-$C_6$-alkyl,
where the substituents R[1'] and R[4'] may be partially or fully substituted by F, Cl and/or Br, in particular —F and/or —Cl, but where R[1'] and R[4'] are not simultaneously CN or cannot simultaneously be fully substituted by F or other halogens, where the substituents R[2'] and R[3'] may be partially or fully substituted by F, Cl and/or Br, in particular —F and/or —Cl, or partially by $NO_2$ or CN
and where, in the substituents R[1'] to R[4'], one or two non-adjacent carbon atoms which are not bonded directly to the heteroatom and are not in the ω-position may be replaced by atoms and/or atom groups selected from the group —O—, —C(O)—, —S—, —S(O)— or —$SO_2$—.

The $C_1$-$C_{20}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl, dodecyl, tridecyl or tetradecyl, optionally fluorinated alkyl groups, for example difluoromethyl, trifluoromethyl, tetrafluoroethyl, pentafluoroethyl, heptafluoropropyl or nonafluorobutyl.

A straight-chain or branched alkenyl having 2 to 20 C atoms, in which a plurality of double bonds may also be present, is, for example, vinyl, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably vinyl, allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

For the purposes of the present invention, fully unsaturated cycloalkyl is also taken to mean aromatic substituents.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group which is substituted by $C_1$- to $C_6$-alkyl groups may in turn also be substituted by F or F and Cl. However, the cycloalkyl groups may likewise be substituted by further functional groups, for example by CN, $SO_2R'$, $SO_2OR'$, $SO_2NH_2$, $C(O)NH_2$ or $C(O)OR'$. R' here has a meaning defined below.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted as described above by F or F and Cl, particularly preferably benzyl or phenylpropyl. However, the phenyl ring or also the alkylene chain may likewise be substituted by further functional groups, for example by CN, $SO_2R'$, $SO_2OR'$, $SO_2NH_2$, $C(O)NH_2$ or $C(O)OR'$.

R' denotes non-, partially or perfluorinated $C_1$- to $C_6$-alkyl, $C_3$- to $C_7$-cycloalkyl, unsubstituted or substituted phenyl. In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CF_3$, $SO_2CH_3$, COOR'', $SO_2X'$, $SO_2NR''_2$ or $SO_3R''$, where X' denotes F, Cl or Br and R'' denotes a non- or partially fluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-nitrophenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In the substituents R, $R^1$ to $R^7$ or R[1'] to R[4'], one or two non-adjacent carbon atoms which are not bonded directly to the heteroatom and are not in the ω-position may also be replaced by atoms and/or atom groups selected from the group —O—, —C(O)—, —S—, —S(O)— or —$SO_2$—.

Without restricting generality, examples of substituents R, $R^1$ to $R^7$ and R[1'] to R[4'] modified in this way are:
—$OCH_3$, —$OCH(CH_3)_2$, —$CH_2OCH_3$, —$CH_2$—$CH_2$—O—$CH_3$, —$C_2H_4OCH(CH_3)_2$, —$C_2H_4C_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$, —$C_4F_9$, —$CF_2CF_2H$, —$CF_2CHFCF_3$, —$CF_2CH(CF_3)_2$, —$C_2F_4N$ $(C_2F_5)C_2F_5$, —$CHF_2$, —$CH_2CF_3$, —$C_2F_2H_3$, —$C_3H_6$, —$CH_2C_3F_7$, —$CH_2C(O)OCH_3$, —$CH_2C(O)CH_3$, —$CH_2C_6H_5$ or —$C(O)C_6H_5$.

The substituents $R^1$ to $R^7$ are each, independently of one another, preferably a straight-chain or branched alkyl group having 1 to 10 C atoms. The substituents $R^1$ and $R^2$, $R^3$ and $R^4$ and $R^5$ and $R^6$ in compounds of the formulae (2) and (3) may be identical or different here.

$R^1$ to $R^7$ are particularly preferably each, independently of one another, methyl, ethyl, n-propyl, isopropyl, n-butyl, sec-butyl, phenyl or cyclohexyl, very particularly preferably methyl, ethyl, n-propyl, isopropyl or n-butyl. However, the substituents R and $R^1$ to $R^7$ may likewise be substituted by further functional groups, for example by CN, $SO_2R'$, $SO_2OR'$, $SO_2NH_2$, $SO_2NR'_2$, $C(O)NH_2$, $C(O)NR'_2$ or $C(O)OR'$. R' here has a meaning defined above.

In accordance with the invention, suitable substituents $R^{1'}$ to $R^{4'}$ of compounds of the formula (4), besides hydrogen, are preferably: CN, $C_1$- to $C_{20}$-, in particular $C_1$- to $C_{12}$-alkyl groups, and saturated or unsaturated, i.e. also aromatic, $C_3$- to $C_7$-cycloalkyl groups, each of which may be substituted by $C_1$- to $C_6$-alkyl groups, in particular phenyl or aryl-$C_1$-$C_6$-alkyl.

The substituents $R^{1'}$ and $R^{4'}$ are each, independently of one another, particularly preferably CN, methyl, ethyl, isopropyl, propyl, butyl, sec-butyl, pentyl, hexyl, octyl, decyl, cyclohexyl, phenyl, phenylpropyl or benzyl. They are very particularly preferably methyl, CN, ethyl, n-butyl or hexyl. In pyrrolidinium or piperidinium compounds, the two substituents $R^{1'}$ and $R^{4'}$ are preferably different.

The substituent $R^{2'}$ or $R^{3'}$ is in each case, independently of one another, in particular hydrogen, dimethylamino, diethylamino, methyl, ethyl, isopropyl, propyl, butyl, sec-butyl, cyclohexyl, phenyl or benzyl. $R^{2'}$ is particularly preferably hydrogen, methyl, ethyl, isopropyl, propyl, butyl, sec-butyl or dimethylamino. $R^{2'}$ and $R^{3'}$ are very particularly preferably hydrogen.

In an embodiment, the alkyl groups as substituents R and $R^1$ to $R^6$ and $R^{1'}$ and $R^{4'}$ of the heterocyclic cations of the formula (4) are different from the alkyl group of the anion in the onium alkylsulfonate.

However, the onium alkylsulfonate prepared in accordance with the invention may also have alkyl groups in the cation which are identical with the alkyl group in the anion, but have not been introduced in accordance with the invention by alkylation.

Up to four substituents of the guanidinium cation $[C(NR^1R^2)(NR^3R^4)—(NR^5R^6)]^+$ may also be connected in pairs in such a way that mono-, bi- or polycyclic cations form.

Without restricting generality, examples of guanidinium cations of this type are:

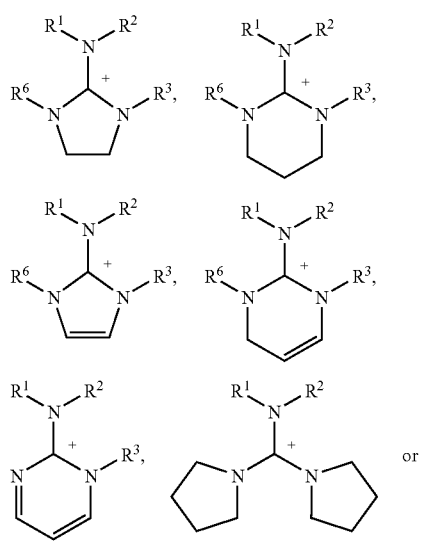

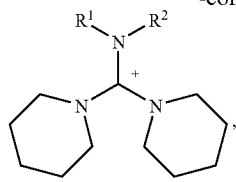

where the substituents $R^1$ to $R^3$ and $R^6$ can have an above-mentioned or particularly preferred meaning.

The carbocycles or heterocycles of the guanidinium cations indicated above may optionally also be substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CF_3$, $SO_2CH_3$, CN, COOR'', $SO_2NR''_2$, $SO_2X'$ or $SO_3R''$, where X' denotes F, Cl or Br and R'' denotes a non- or partially fluorinated $C_1$- to $C_6$-alkyl or $C_3$- to $C_7$-cycloalkyl as defined for R', or by substituted or unsubstituted phenyl.

Up to four substituents of the uronium or thiouronium cation $[(R^1R^2N)—C(=YR^7)(NR^3R^4)]^+$ may also be connected in pairs in such a way that mono-, bi- or polycyclic cations form.

Without restricting generality, examples of cations of this type are indicated below:

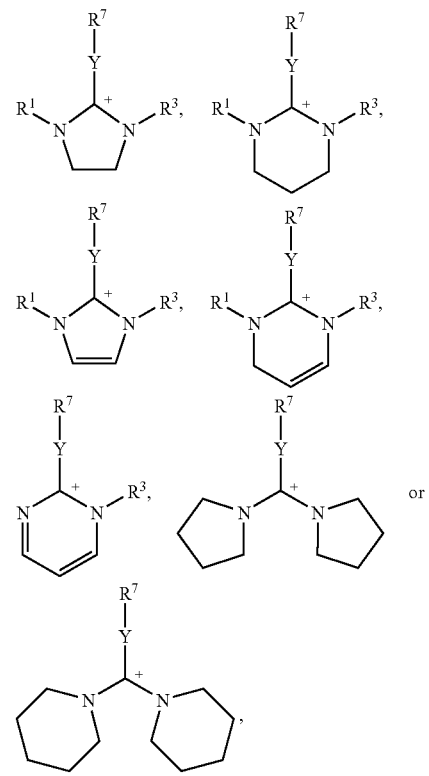

where Y and the substituents $R^1$, $R^3$ and $R^7$ can have an above-mentioned or particularly preferred meaning.

The carbocycles or heterocycles of the uronium or thiouronium cations indicated above may optionally also be substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CF_3$, $SO_2CH_3$, COOR'', $SO_2NR''_2$, $SO_2X'$ or $SO_3R''$, where X' denotes F, Cl or Br and R'' denotes a non-, partially or perfluorinated $C_1$- to $C_6$-alkyl or $C_3$- to $C_7$-cycloalkyl as defined for R', or by substituted or unsubstituted phenyl.

However, the substituents $R^{1'}$ to $R^{4'}$ may likewise be substituted by further functional groups, for example by CN, $SO_2R'$, $SO_2OR'$ or COOR'. R' here has a meaning defined above.

HetN$^+$ of the formula (4) is preferably

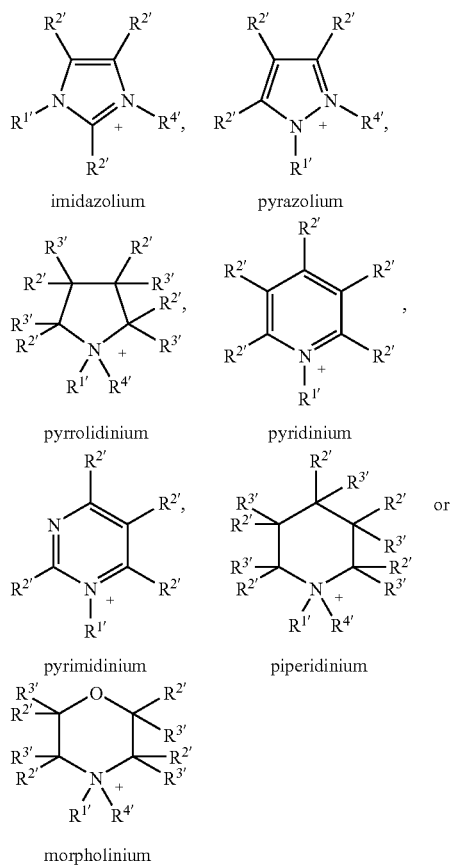

where the substituents $R^{1'}$ to $R^{4'}$ each, independently of one another, have a meaning described above.

HetN$^+$ is particularly preferably imidazolium, pyrrolidinium or pyridinium, as defined above, where the substituents $R^{1'}$ to $R^{4'}$ each, independently of one another, have a meaning described above.

In the said formulae (1) to (4), Hal may in accordance with the invention be replaced by carboxylates, as defined above. The choice of the anion does not restrict the choice of the cation.

The symmetrically substituted dialkyl sulfite employed in the processes according to the invention is preferably a dialkyl sulfite containing a straight-chain or branched alkyl group having 1-10 C atoms, preferably having 1-4 C atoms, particularly preferably having 1-2 C atoms. The alkyl group is preferably a straight-chain or branched alkyl group having 1-4 C atoms, such as, for example, methyl, ethyl, isopropyl, propyl, butyl, sec-butyl or tert-butyl. The alkyl group is preferably methyl or ethyl.

Examples of symmetrically substituted dialkyl sulfites are dimethyl sulfite, diethyl sulfite, di-(n-propyl) sulfite, di-(isopropyl) sulfite, di-(n-butyl) sulfite or di-(sec-butyl) sulfite. Preference is given to the use of dimethyl sulfite or diethyl sulfite.

The symmetrical dialkyl sulfites employed are generally commercially available or can be prepared by synthetic methods as are known from the literature, for example in the standard works, such as Houben-Weyl, Methoden der organischen Chemie [Methods of Organic Chemistry], Georg-Thieme-Verlag, Stuttgart, or Richard C. Larock, Comprehensive Organic Transformations, 2nd Edition, Wiley-VCH, New York, 1999, or from the article by W. Voss and E. Blanke, Justus Liebigs Ann. Chem., 485 (1931), pp. 258-279. Use can also be made here of variants known per se which are not mentioned here in greater detail.

The asymmetrically substituted dialkyl sulfite employed is preferably a dialkyl sulfite containing a straight-chain or branched alkyl group having 1 to 10 C atoms and a methyl or ethyl group as second alkyl group, preferably containing an alkyl group having 3-8 C atoms. Examples of asymmetrically substituted dialkyl sulfites are methyl propyl sulfite, methyl butyl sulfite, ethyl butyl sulfite, methyl pentyl sulfite, ethyl pentyl sulfite, methyl hexyl sulfite, ethyl hexyl sulfite, methyl heptyl sulfite, ethyl heptyl sulfite, methyl octyl sulfite or ethyl octyl sulfite.

The asymmetrical dialkyl sulfites employed can be prepared by synthetic methods as are known from the literature, for example in the standard works, such as Houben-Weyl, Methoden der organischen Chemie [Methods of Organic Chemistry], Georg-Thieme-Verlag, Stuttgart, or Richard C. Larock, Comprehensive Organic Transformations, 2nd Edition, Wiley-VCH, New York, 1999, or from the article by W. Voss and E. Blanke, Justus Liebigs Ann. Chem., 485 (1931), pp. 258-279, or by V. M. Pavlov, J. Gen. Chem. USSR (Eng. transl.), 41 (1971), pp. 2559-2561. Use can also be made here of variants known per se which are not mentioned here in greater detail.

A general scheme summarises the process according to the invention, where the arrow in the case of the alkyl-halogen compound forming represents a symbol for the volatility of the compound:

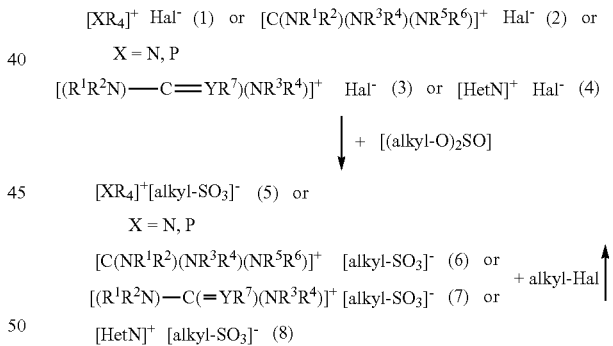

The substituents R, $R^1$ to $R^7$ and HetN$^+$ of the compounds of the formulae (1) to (8) correspond to the meanings as described above.

The reaction with dialkyl sulfites is carried out at temperatures between 50 and 170° C., preferably at temperatures between 60 and 130° C. and particularly preferably at temperatures between 100 and 120° C. The temperatures from 50° C. here correspond to the temperature of the heating source, for example of the oil bath. The choice of the optimum reaction temperature depends here on the level of the excess of the dialkyl sulfite and on the type of halide and dialkyl sulfite employed. Iodides are more reactive than chlorides, and in general higher temperatures and longer reaction times are necessary in the case of dialkyl sulfites containing relatively long alkyl chains.

No solvent is required. However, it is also possible to employ solvents, for example dimethoxyethane, acetonitrile, acetone, tetrahydrofuran, dimethylformamide, dimethyl sulfoxide, dioxane, propionitrile, dichloromethane or mixtures with one another.

The reaction is carried out with an excess or equimolar amount of dialkyl sulfite, preferably with an excess of dialkyl sulfite.

Alternatively, onium salts with alkylsulfonate anions can be prepared by direct alkylation of organic bases using dialkyl sulfites. The alkylation of aniline, dimethylaniline and pyridine using dimethyl sulfite with formation of the corresponding methylsulfonates is described in the article by W. Voss and E. Blanke, Justus Liebigs Ann. Chem., 485 (1931), pp. 258-279. The disadvantage of this method is the formation of onium compounds which have the same alkyl group both in the cation and in the anion and thus restrict the possible variety of the substitution patterns. In addition, toxic sulfur dioxide forms in equimolar amounts in this reaction.

The present invention likewise relates to onium alkylsulfonates prepared by the process according to the invention. Some of the compounds are known. Use of the process according to the invention simplifies access to these compounds and thus increases the possibility of utilisation of these compounds.

In addition, the present invention likewise relates to onium alkylsulfonates of the formula (9), obtainable by the process according to the invention $$[Kt]^+[alkyl\text{-}SO_3]^- \quad (9)$$

where

Kt denotes $[(R^1R^2N)\text{—}C(=\!SR^7)(NR^3R^4)]$ or [HetN], where [HetN] is selected from the group comprising

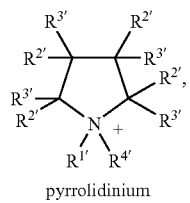
pyrrolidinium

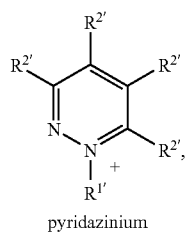
pyridazinium

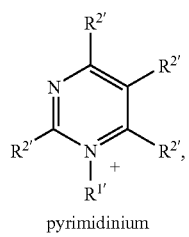
pyrimidinium

-continued

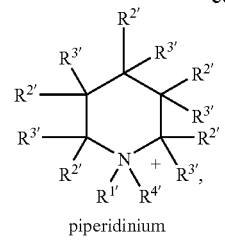
piperidinium

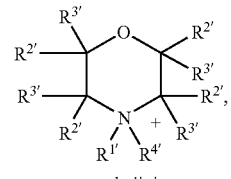
morpholinium

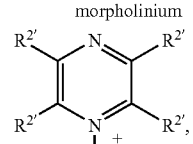
pyrazinium

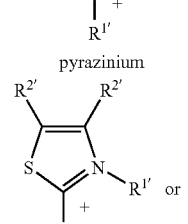
thiazolium

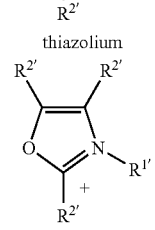
oxazolium and where alkyl denotes straight-chain or branched alkyl groups having 1-10 C atoms, preferably having 1-8 C atoms, where the alkyl groups may be partially or fully substituted by F, Cl and/or Br, in particular F and/or Cl, or partially by $NO_2$ or CN, and where, in the alkyl groups, one or two non-adjacent carbon atoms which are not bonded directly to the heteroatom and are not in the ω-position may be replaced by atoms and/or atom groups selected from the group —O—, —C(O)—, —S—, —S(O)— or —$SO_2$— and where $R^1$ to $R^7$ and $R^{1\prime}$ to $R^{4\prime}$ have the above-mentioned meaning, with the proviso that in the case of [HetN] as cation Kt, alkyl does not denote trifluoromethyl. Compounds of this type have hitherto not been described or characterised in greater detail.

It goes without saying to the person skilled in the art that all substituents mentioned above, such as, for example, H, N, O, Cl, F, may be replaced by the corresponding isotopes.

The present invention likewise relates to the use of the compounds of the formula (9) according to the invention as solvent, solvent additive, heat-transfer medium, phase-transfer catalyst, as extractant, as additive, as surface-active substance, as electrolyte in electrochemical cells, as modifier or as plasticiser.

In the case of the use as solvent or solvent additive, the compounds according to the invention are suitable in any type of reaction known to the person skilled in the art, for example reactions catalysed by transition metals, enzymes or other biocatalysts, such as, for example, hydroformylation reactions, oligomerisation reactions, C—C bond formation reactions, for example the Heck coupling, but also esterifications, isomerisation reactions or reactions for the formation of amide bonds.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. on a Bruker ARX 400 spectrometer with a 5 mm $^1$H/BB broad-band head with deuterium lock, unless indicated otherwise in the examples. The measurement frequencies of the various nuclei are: $^1$H, 400.13 MHz and $^{31}$P: 161.98 MHz. The referencing method is indicated separately for each spectrum or each data set.

EXAMPLES

Example 1

1-Hexyl-3-methylimidazolium methanesulfonate

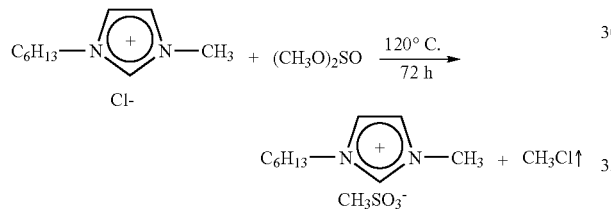

A mixture of 10.84 g (53.5 mmol) of 1-hexyl-3-methylimidazolium chloride and 11.21 g (101.8 mmol) of dimethyl sulfite is stirred at 120° C. (temperature of the oil bath) for 72 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 120° C. (temperature of the oil bath), giving 14.0 g of liquid 1-hexyl-3-methylimidazolium methanesulfonate. The yield is virtually quantitative. The product is investigated by means of NMR spectroscopy.

$^1$H NMR (reference: TMS; solvent: CD$_3$CN), ppm: 0.86 m (CH$_3$); 1.28 m (3CH$_2$); 1.81 m (CH$_2$); 2.44 s (CH$_3$); 3.84 s (CH$_3$); 4.13 t (CH$_2$); 7.39 d,d (CH); 7.42 d,d (CH); 8.81 br. s. (CH); $^3J_{H,H}$=7.1 Hz; J$_{H,H}$=1.5 Hz.

Example 2

1-Hexyl-3-methylimidazolium methanesulfonate

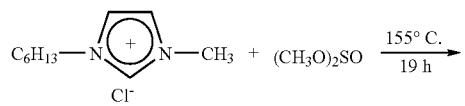

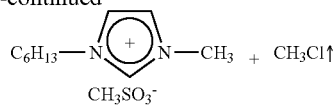

A mixture of 8.43 g (41.6 mmol) of 1-hexyl-3-methylimidazolium chloride and 4.58 g (41.6 mmol) of dimethyl sulfite is stirred at 155° C. (temperature of the oil bath) for 19 hours under an inert-gas atmosphere (nitrogen) in a 50 ml round-bottomed flask with reflux condenser. The end of the reaction was determined by NMR measurement. The product is pumped off over the course of 2 hours in vacuo at 13.3 Pa and 100° C. (temperature of the oil bath), giving 10.0 g of liquid 1-hexyl-3-methylimidazolium methanesulfonate. The yield is 91.7%. The product is investigated by means of NMR spectroscopy.

$^1$H NMR (reference: TMS; solvent: CD$_3$CN), ppm: 0.84 m (CH$_3$); 1.26 m (3CH$_2$); 1.80 m (CH$_2$); 2.45 s (CH$_3$); 3.86 s (CH$_3$); 4.17 t (CH$_2$); 7.48 m (CH); 7.50 m (CH); 9.30 br. s. (CH); $^3J_{H,H}$=7.1 Hz.

Example 3

1-Hexyl-3-methylimidazolium ethanesulfonate

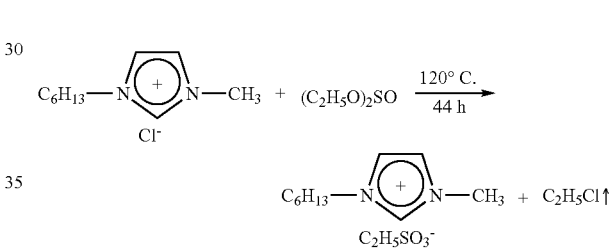

A mixture of 11.84 g (58.4 mmol) of 1-hexyl-3-methylimidazolium chloride and 12.11 g (87.6 mmol) of diethyl sulfite is stirred at 120° C. (temperature of the oil bath) for 44 hours under an inert-gas atmosphere (nitrogen) in a sealed reaction vessel with pressure valve for 1-1.5 bar above atmospheric pressure. The end of the reaction is determined by NMR measurement. The product is pumped off over the course of 3 hours in vacuo at 13.3 Pa and 120° C. (temperature of the oil bath), giving 16.1 g of liquid 1-hexyl-3-methylimidazolium ethanesulfonate. The yield is virtually quantitative. The product is investigated by means of NMR spectroscopy.

$^1$H NMR (reference: TMS; solvent: CD$_3$CN), ppm: 0.87 m (CH$_3$); 1.17 t (CH$_3$); 1.29 m (3CH$_2$); 1.82 m (CH$_2$); 2.59 q (CH$_2$); 3.87 s (CH$_3$); 4.17 t (CH$_2$); 7.44 m (CH); 7.47 m (CH); 9.11 br. s. (CH); $^3J_{H,H}$=7.1 Hz; $^3J_{H,H}$=7.4 Hz.

Example 4

1-Ethyl-3-methylimidazolium methanesulfonate

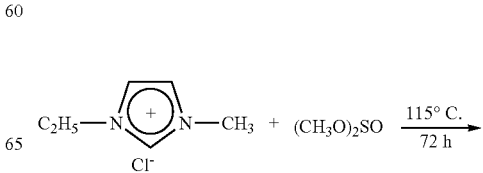

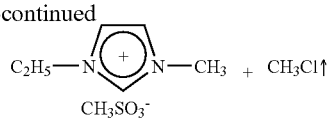

A mixture of 10.64 g (72.6 mmol) of 1-ethyl-3-methylimidazolium chloride and 14.39 g (130.7 mmol) of dimethyl sulfite is stirred at 110-115° C. (temperature of the oil bath) for 72 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 115° C. (temperature of the oil bath), giving 14.78 g of liquid 1-ethyl-3-methylimidazolium methanesulfonate. The yield is virtually quantitative. The residual chloride content is less than 5 ppm. The product is investigated by means of NMR spectroscopy.

$^1$H NMR (reference: TMS; solvent: CD$_3$CN), ppm: 1.41 t (CH$_3$); 2.44 s (CH$_3$); 3.85 s (CH$_3$); 4.19 q (CH$_2$); 7.51 d,d (CH); 7.57 d,d (CH); 9.26 br. s. (CH); $^3J_{H,H}$=7.4 Hz; $J_{H,H}$=1.5 Hz.

Example 5

Trihexyltetradecylphosphonium Methanesulfonate

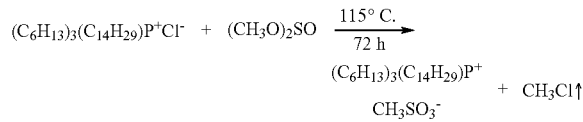

A mixture of 6.42 g (12.36 mmol) of trihexyltetradecylphosphonium chloride and 4.28 g (38.86 mmol) of dimethyl sulfite is stirred at 110-115° C. (temperature of the oil bath) for 72 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 115° C. (temperature of the oil bath), giving 7.06 g of liquid trihexyltetradecylphosphonium methanesulfonate. The yield is virtually quantitative. The residual chloride content is less than 5 ppm. The product is investigated by means of NMR spectroscopy.

$^1$H NMR (reference: TMS; solvent: CD$_3$CN), ppm: 0.84-0.92 m (4-CH$_3$), 1.24-1.36 m (16CH$_2$), 1.36-1.56 m (8CH$_2$), 2.04-2.15 m (4-CH$_2$); 2.44 s (CH$_3$).

$^{31}$P {$^1$H} NMR (reference: 85% H$_3$PO$_4$— external; solvent: CD$_3$CN), ppm: 33.3

Example 6

1-Butylpyridinium methanesulfonate

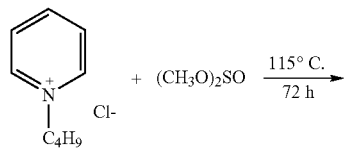

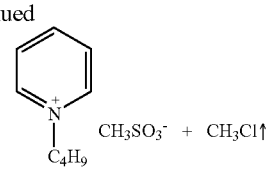

A mixture of 11.88 g (69.2 mmol) of 1-butylpyridinium chloride and 13.69 g (124.3 mmol) of dimethyl sulfite is stirred at 110-115° C. (temperature of the oil bath) for 72 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 115° C. (temperature of the oil bath), giving 15.51 g of 1-butylpyridinium methanesulfonate as a solid. The melting point is 91-92° C. The yield is 96.9%. The residual chloride content is less than 5 ppm. The product is investigated by means of NMR spectroscopy.

$^1$H NMR (reference: TMS; solvent: CD$_3$CN), ppm: 0.93 t (CH$_3$); 1.36 m (CH$_2$); 1.93 m (CH$_2$); 2.43 s (CH$_3$); 4.59 t (CH$_2$); 8.04 m (2CH); 8.50 t (CH); 8.90 d (2CH); $^3J_{H,H}$=7.4 Hz; $^3J_{H,H}$=7.6 Hz; $^3J_{H,H}$=7.9 Hz; $^3J_{H,H}$=6.6 Hz.

Elemental analysis: found, %: C, 51.74; H, 7.34; N, 6.07; S, 13.92; calculated for C$_{10}$H$_{17}$NO$_3$S, %: C, 51.93; H, 7.41; N, 6.06; S, 13.86.

Example 7

1-Butyl-1-methylpyrrolidinium methanesulfonate

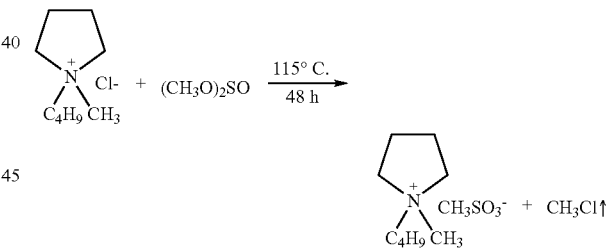

A mixture of 11.20 g (63.0 mmol) of 1-butyl-1-methylpyrrolidinium chloride and 13.0 g (118.0 mmol) of dimethyl sulfite is stirred at 110-115° C. (temperature of the oil bath) for 48 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 115° C. (temperature of the oil bath), giving 14.9 g of 1-butyl-1-methylpyrrolidinium methanesulfonate as a solid. The melting point is 59-60° C. The residual chloride content is less than 5 ppm. The yield is virtually quantitative. The product is investigated by means of NMR spectroscopy.

$^1$H NMR (reference: TMS; solvent: CD$_3$CN), ppm: 0.94 t (CH$_3$); 1.36 m (CH$_2$); 1.70 m (CH$_2$); 2.13 m (2CH$_2$); 2.40 s (CH$_3$); 2.97 s (CH$_3$); 3.29 m (CH$_2$); 3.45 m (2CH$_2$); $^3J_{H,H}$=7.4 Hz.

Elemental analysis: found, %: C, 50.29; H, 9.97; N, 5.90; S, 13.52; calculated for $C_{10}H_{23}NO_3S$, %: C, 50.60; H, 9.77; N, 5.90; S, 13.51.

Example 8

N,N,N',N'-tetramethyl-5-ethylthiouronium methanesulfonate

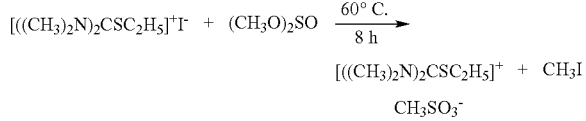

A mixture of 2.72 g (9.44 mmol) of N,N,N',N'-tetramethyl-5-ethylthiouronium iodide and 1.04 g (9.44 mmol) of dimethyl sulfite is stirred at 60° C. (temperature of the oil bath) for 8 hours under an inert-gas atmosphere (nitrogen) in a sealed reaction vessel. The end of the reaction is determined by NMR measurement. The product is pumped off over the course of 1 hour in vacuo at 13.3 Pa and 60° C. (temperature of the oil bath), giving 2.39 g of N,N,N',N'-tetramethyl-5-ethylthiouronium methanesulfonate as a solid. The melting point is 75-76° C. The yield is virtually quantitative. The product is investigated by means of NMR spectroscopy.

$^1$H NMR (reference: TMS; solvent: $CD_3CN$), ppm: 1.29 t ($CH_3$); 2.39 s ($CH_3$); 3.01 q ($CH_2$); 3.23 s ($4CH_3$); $^3J_{H,H}$=7.5 Hz.

Elemental analysis: found, %: C, 36.95; H, 7.92; N, 10.78; calculated for $C_8H_{20}N_2O_3S_2$, %: C, 37.48; H, 7.86; N, 10.93.

Example 9

Tetrabutylammonium Methanesulfonate

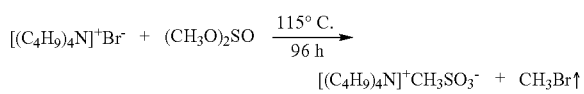

A mixture of 12.94 g (40.14 mmol) of tetrabutylammonium bromide and 5.15 g (46.76 mmol) of dimethyl sulfite is stirred at 110-115° C. (temperature of the oil bath) for 96 hours under an inert-gas atmosphere (nitrogen) in a sealed reaction vessel with pressure valve for 1-1.5 bar above atmospheric pressure. The end of the reaction is determined by NMR measurement. The product is pumped off over the course of 5 hours in vacuo at 13.3 Pa and 115° C. (temperature of the oil bath), giving 13.53 g of tetrabutylammonium methanesulfonate as a solid. The melting point is 83-84° C. The yield is virtually quantitative. The residual bromide content is less than 5 ppm. The product is investigated by means of NMR spectroscopy.

$^1$H NMR (reference: TMS; solvent: $CD_3CN$), ppm: 0.95 t ($CH_3$); 1.34 t,q ($CH_2$); 1.60 m ($CH_2$); 2.39 s ($CH_3$); 3.11 m ($CH_2$); $^3J_{H,H}$=7.4 Hz.

Elemental analysis: found, %: C, 60.47; H, 11.90; N, 4.18; S, 9.60; calculated for $C_{17}H_{39}NO_3S$, %: C, 60.49; H, 11.65; N, 4.15; S, 9.50.

Example 10

Tetrabutylammonium methanesulfonate

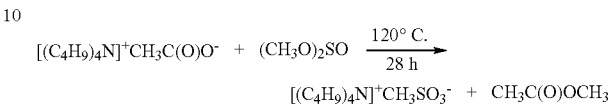

A mixture of 0.56 g (1.86 mmol) of tetrabutylammonium acetate and 0.41 g (3.72 mmol) of dimethyl sulfite is stirred at 120° C. (temperature of the oil bath) for 28 hours under an inert-gas atmosphere (nitrogen) in a sealed reaction vessel. The end of the reaction is determined by NMR measurement. The product is pumped off over the course of 2 hours in vacuo at 13.3 Pa and 70° C. (temperature of the oil bath), giving 0.61 g of tetrabutylammonium methanesulfonate as a solid. The melting point is 84-85° C. The yield is virtually quantitative. The product is investigated by means of NMR spectroscopy.

$^1$H NMR (reference: TMS; solvent: $CD_3CN$), ppm: 0.95 t ($CH_3$); 1.34 t,q ($CH_2$); 1.60 m ($CH_2$); 2.42 s ($CH_3$); 3.11 m ($CH_2$); $^3J_{H,H}$=7.4 Hz.

Example 11

1,3-Dimethylimidazolium methanesulfonate

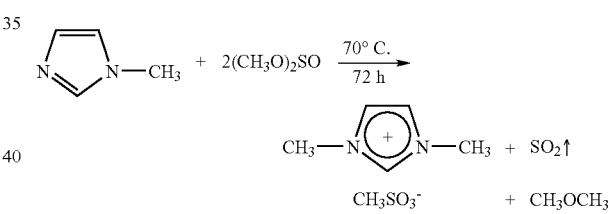

A mixture of 6.64 g (80.9 mmol) of N-methylimidazole and 14.39 g (161.7 mmol) of dimethyl sulfite is stirred at 70° C. (temperature of the oil bath) for 72 hours under an inert-gas atmosphere (nitrogen) in a 100 ml round-bottomed flask with reflux condenser. The end of the reaction is determined by NMR measurement. The product is pumped off over the course of 2 hours in vacuo at 13.3 Pa and 80° C. (temperature of the oil bath), giving 15.22 g of 1,3-dimethylimidazolium methanesulfonate as a solid. The melting point is 72-73° C. The yield is 98%. The product is investigated by means of NMR spectroscopy.

$^1$H NMR (reference: TMS; solvent: $CD_3CN$), ppm: 2.44 s ($CH_3$); 3.84 s ($2CH_3$); 7.45 d ($2CH$); 9.12 br. s. ($CH$); $^4J_{H,H}$=1.6 Hz.

Elemental analysis: found, %: C, 37.27; H, 6.35; N, 14.76; S, 16.40; calculated for $C_6H_{12}N_2O_3S$, %: C, 37.49; H, 6.29; N, 14.57; S, 16.68.

The invention claimed is:
1. A process for the preparation of an onium alkylsulfonate, comprising reacting an onium halide or carboxylate with a symmetrically substituted dialkyl sulfite or with an asymmetrically substituted dialkyl sulfite at temperatures of 50 to 170° C., whereby the onium alkylsulfonate is produced, wherein the halide is an ammonium halide, phosphonium halide, thiouronium halide, guanidinium halide or a halide with a heterocyclic cation, wherein the halide with a heterocyclic cation has formula (4)

[HetN]⁺Hal⁻     (4), where

Hal denotes Cl, Br or I,

HetN⁺ denotes a heterocyclic cation of the formula

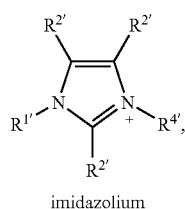
imidazolium

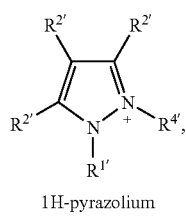
1H-pyrazolium

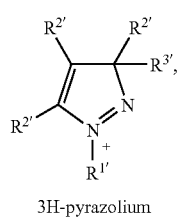
3H-pyrazolium

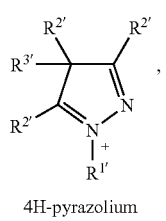
4H-pyrazolium

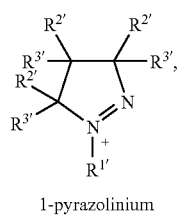
1-pyrazolinium

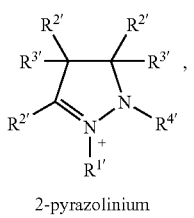
2-pyrazolinium

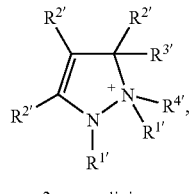
3-pyrazolinium

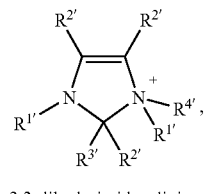
2,3-dihydroimidazolinium

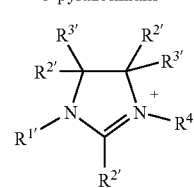
4,5-dihydroimidazolinium

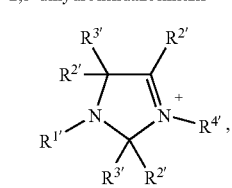
2,5-dihydroimidazolinium

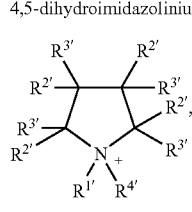
pyrrolidinium

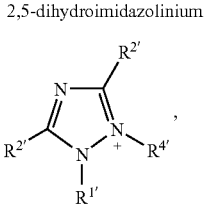
1,2,4-triazolium

-continued

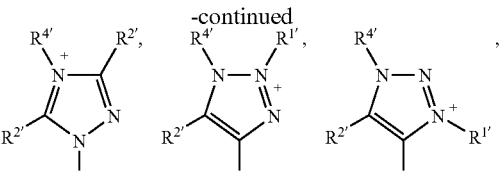
1,2,4-triazolium   1,2,3-triazolium   1,2,3-triazolium

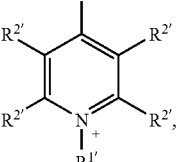
pyridinium

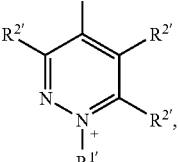
pyridazinium

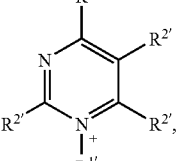
pyrimidinium

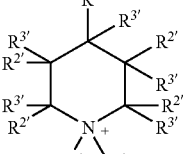
piperidinium

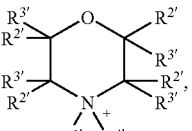
morpholinium

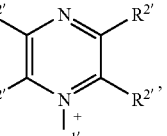
pyrazinium

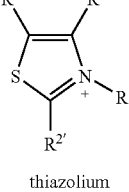
thiazolium or

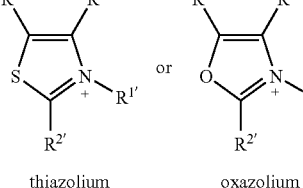
oxazolium $R^{1'}$ to $R^{4'}$ each, independently of one another, denote
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms, or
aryl-$C_1$-$C_6$-alkyl,
where the substituents $R^{1'}$ and $R^{4'}$ may be partially or fully substituted by F, Cl and/or Br, but where $R^{1'}$ and $R^{4'}$ are not simultaneously CN or cannot simultaneously be fully substituted by F or other halogens,
where the substituents $R^{2'}$ and $R^{3'}$ may be partially or fully substituted by F, Cl and/or Br, or partially by $NO_2$ or CN, and
where, in the substituents $R^{1'}$ to $R^{4'}$, one or two non-adjacent carbon atoms which are not bonded directly to the heteroatom and are not in the ω-position may be replaced by —O—, —C(O)—, —S—, —S(O)— or —SO₂—, where the halides are selected from the group consisting of chlorides, bromides, iodides, and uronium iodide.

2. The process according to claim 1, wherein the reaction is carried out with a symmetrically substituted dialkyl sulfite, where the alkyl group has 1 to 10 C atoms.

3. The process according to claim 1, wherein the reaction is carried out with an asymmetrically substituted dialkyl sulfite, where one alkyl group has 1 to 10 C atoms and the second alkyl group denotes methyl or ethyl.

4. The process according to claim 1, wherein the halide is a halide with a heterocyclic cation.

5. A process for the preparation of an onium alkylsulfonate, comprising reacting an onium halide or carboxylate with a symmetrically substituted dialkyl sulfite or with an asymmetrically substituted dialkyl sulfite at temperatures of 50 to 170° C., whereby the onium alkylsulfonate is produced, wherein the carboxylate is an ammonium acetate, phosphonium acetate, a guanidinium acetate or an acetate with a heterocyclic cation, wherein the heterocyclic cation is HetN⁺, which is of formula

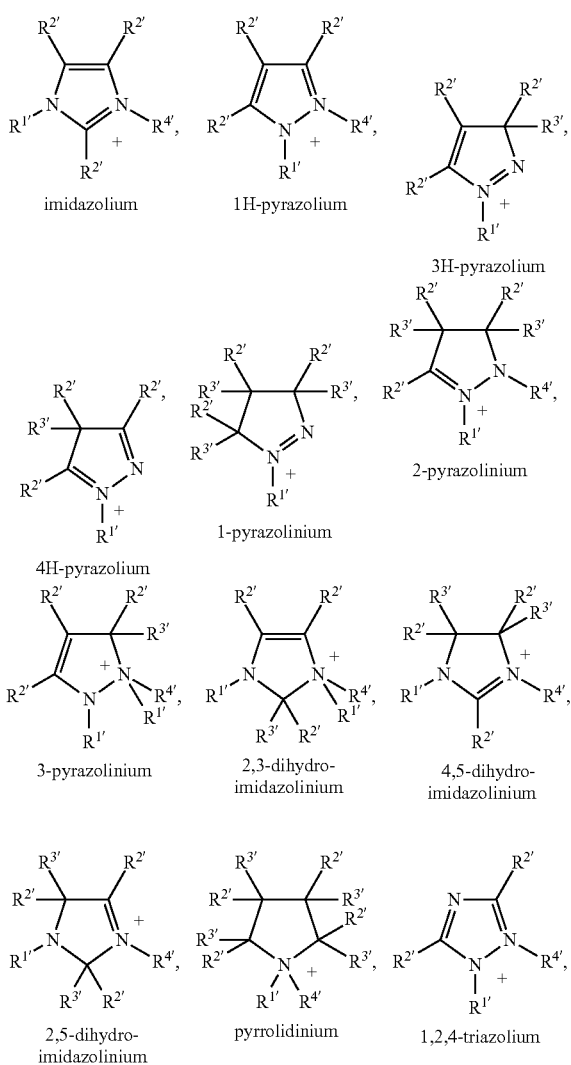

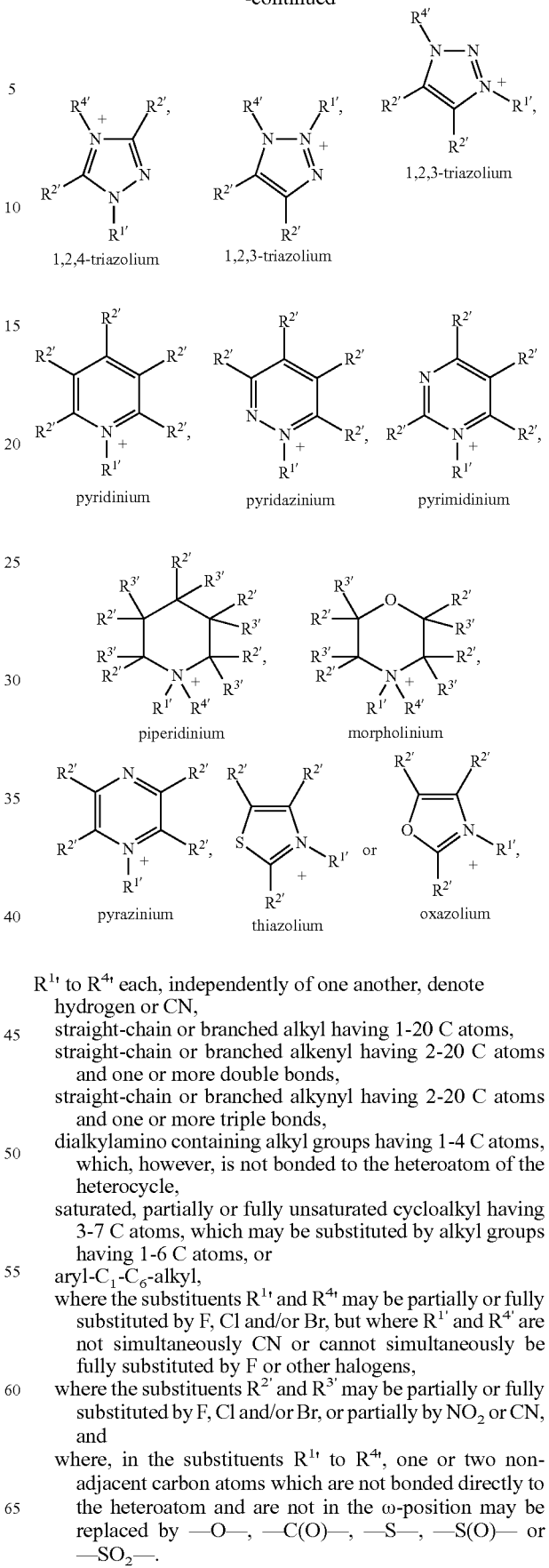

$R^{1'}$ to $R^{4'}$ each, independently of one another, denote hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms, or
aryl-$C_1$-$C_6$-alkyl,
where the substituents $R^{1'}$ and $R^{4'}$ may be partially or fully substituted by F, Cl and/or Br, but where $R^{1'}$ and $R^{4'}$ are not simultaneously CN or cannot simultaneously be fully substituted by F or other halogens,
where the substituents $R^{2'}$ and $R^{3'}$ may be partially or fully substituted by F, Cl and/or Br, or partially by $NO_2$ or CN, and
where, in the substituents $R^{1'}$ to $R^{4'}$, one or two non-adjacent carbon atoms which are not bonded directly to the heteroatom and are not in the ω-position may be replaced by —O—, —C(O)—, —S—, —S(O)— or —SO₂—.

6. The process according to claim 1, wherein the halide has formula (1)

where
X denotes N, or P,
Hal denotes Cl, Br or I, and
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds, or
straight-chain or branched alkynyl having 2-20 C atoms and one or more triple bonds, saturated, partially or fully unsaturated cycloalkyl having 3-7 C atoms, which may be substituted by alkyl groups having 1-6 C atoms,
where one or more R may be partially substituted by Cl, Br and/or CN or partially or fully by F, or F and Cl, or F and Br, or F, Cl and Br, but where all four or three R cannot be fully substituted by halogens, and
where one or two non-adjacent carbon atoms of the R which are not in the α- or ω-position may be replaced by —O—, —C(O)—, —S—, —S(O)— or —SO$_2$—.

7. The process according to claim 1, wherein the halide has formula (2)

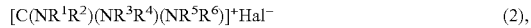

where
Hal denotes Cl, Br or I, and
$R^1$ to $R^6$ each, independently of one another, denote
hydrogen or CN,
straight-chain or branched alkyl having 1 to 20 C atoms,
straight-chain or branched alkenyl having 2-20 C atoms and one or more double bonds, or
straight-chain or branched alkynyl having 2-20 C atoms and one or more triple bonds, saturated, partially or fully unsaturated cycloalkyl having 3-7 C atoms, which may be substituted by alkyl groups having 1-6 C atoms,
where one or more of the substituents $R^1$ to $R^6$ may be partially substituted by $NO_2$, CN, Cl and/or Br, partially or fully by F, or F and Cl, or F and Br or F, Cl and Br, but where all substituents on an N atom cannot be fully substituted by halogens,
where the substituents $R^1$ to $R^6$ may be connected to one another in pairs by a single or double bond, and
where, in the substituents $R^1$ to $R^6$, one or two non-adjacent carbon atoms which are not bonded directly to the heteroatom and are not in the ω-position may be replaced by —O—, —C(O)—, —S—, —S(O)— or —SO$_2$—.

8. The process according to claim 1, wherein the halide has formula (3)

where
Y denotes O, or S,
Hal denotes Br or I, with the proviso that, in the case where Y=O, Hal=I, and
$R^1$ to $R^4$
and $R^7$ each, independently of one another, denote
hydrogen or CN, where hydrogen is excluded for $R^7$,
straight-chain or branched alkyl having 1 to 20 C atoms,
straight-chain or branched alkenyl having 2-20 C atoms and one or more double bonds, or
straight-chain or branched alkynyl having 2-20 C atoms and one or more triple bonds, saturated, partially or fully unsaturated cycloalkyl having 3-7 C atoms, which may be substituted by alkyl groups having 1-6 C atoms,
where one or more of the substituents $R^1$ to $R^4$ and $R^7$ may be partially or fully substituted by F, Cl and/or Br, or partially by CN, but where all substituents on an N atom cannot be fully substituted by halogens,
where the substituents $R^1$ to $R^4$ and $R^7$ may be connected to one another in pairs by a single or double bond, and
where, in the substituents $R^1$ to $R^4$ and $R^7$, one or two non-adjacent carbon atoms which are not bonded directly to the heteroatom and are not in the ω-position may be replaced by —O—, —C(O)—, —S—, —S(O)— or —SO$_2$—.

9. The process according to claim 1, wherein the halide has formula (4)

where
Hal denotes Cl, Br or I,
HetN$^+$ denotes a heterocyclic cation of the formula

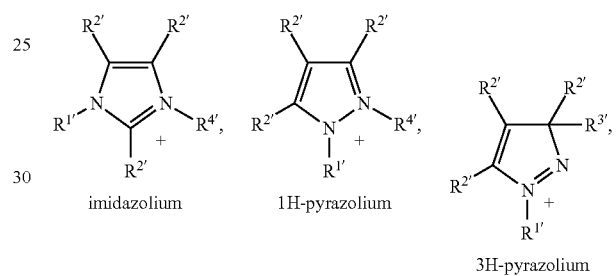

imidazolium  1H-pyrazolium  3H-pyrazolium

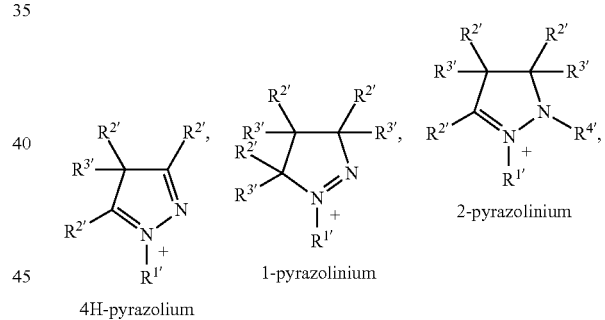

4H-pyrazolium  1-pyrazolinium  2-pyrazolinium

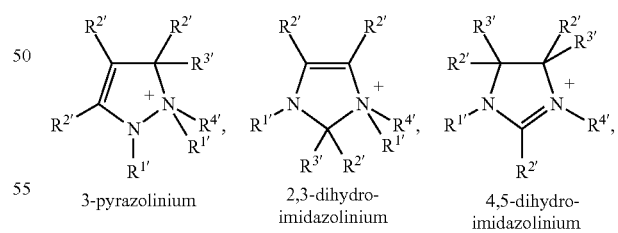

3-pyrazolinium  2,3-dihydro-imidazolinium  4,5-dihydro-imidazolinium

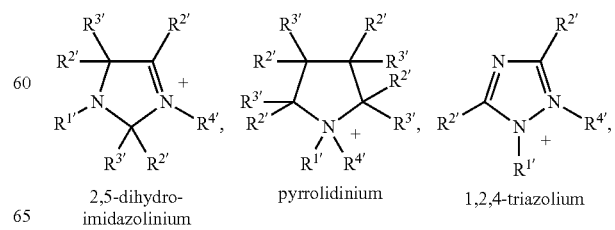

2,5-dihydro-imidazolinium  pyrrolidinium  1,2,4-triazolium

-continued

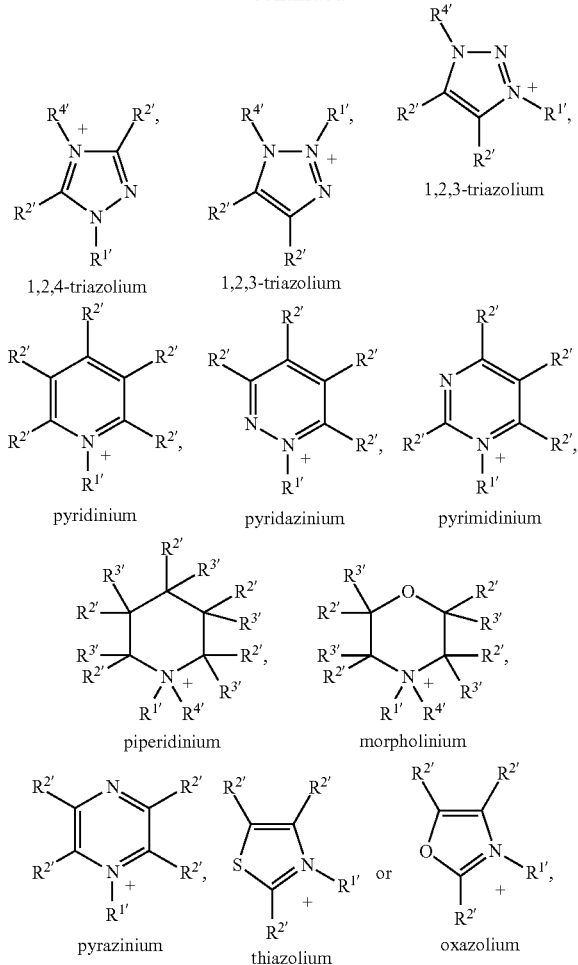

R$^{1\prime}$ to R$^{4\prime}$ each, independently of one another, denote
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms, or
aryl-C$_1$-C$_6$-alkyl,
where the substituents R$^{1\prime}$ and R$^{4\prime}$ may be partially or fully substituted by F, Cl and/or Br, but where R$^{1\prime}$ and R$^{4\prime}$ are not simultaneously CN or cannot simultaneously be fully substituted by F or other halogens,
where the substituents R$^{2\prime}$ and R$^{3\prime}$ may be partially or fully substituted by F, Cl and/or Br, or partially by NO$_2$ or CN, and
where, in the substituents R$^{1\prime}$ to R$^{4\prime}$, one or two non-adjacent carbon atoms which are not bonded directly to the heteroatom and are not in the ω-position may be replaced by —O—, —C(O)—, —S—, —S(O)— or —SO$_2$—.

10. A process for the preparation of an onium alkylsulfonate, comprising reacting an onium halide or carboxylate with a symmetrically substituted dialkyl sulfite or with an asymmetrically substituted dialkyl sulfite at temperatures of 50 to 170° C., whereby the onium alkylsulfonate is produced, wherein the reaction of the halide with the dialkyl sulfite is carried out without a solvent,
wherein the halide is an ammonium halide, phosphonium halide, thiouronium halide, guanidinium halide or a halide with a heterocyclic cation,
wherein the halide with a heterocyclic cation has formula (4)

$$[HetN]^+Hal^- \qquad (4),$$

where
Hal denotes Cl, Br or I,
HetN$^+$ denotes a heterocyclic cation of the formula

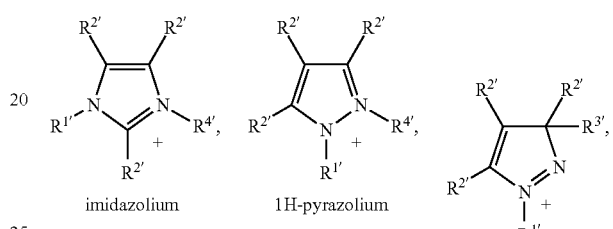

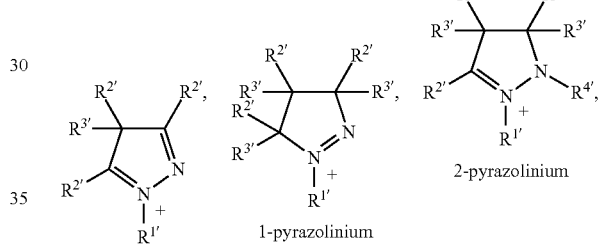

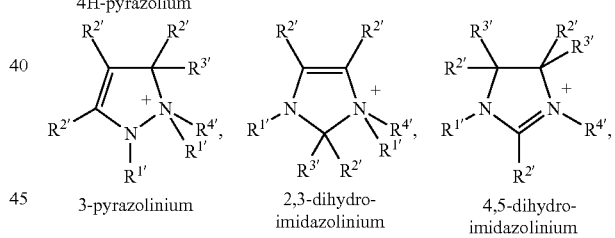

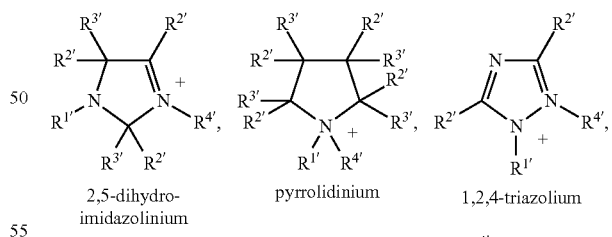

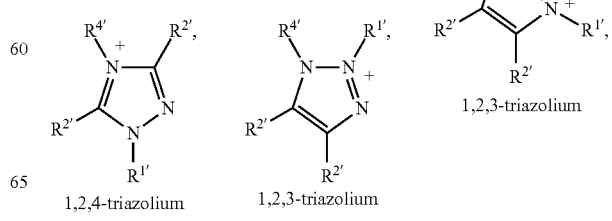

-continued

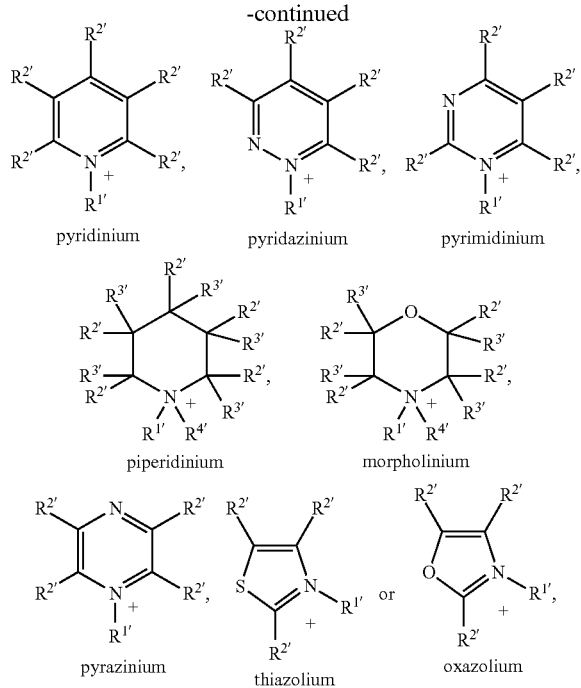

pyridinium pyridazinium pyrimidinium
piperidinium morpholinium
pyrazinium thiazolium oxazolium R$^{1\prime}$ to R$^{4\prime}$ each, independently of one another, denote
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms, or
aryl-C$_1$-C$_6$-alkyl,
where the substituents R$^{1\prime}$ and R$^{4\prime}$ may be partially or fully substituted by F, Cl and/or Br, but where R$^{1\prime}$ and R$^{4\prime}$ are not simultaneously CN or cannot simultaneously be fully substituted by F or other halogens,
where the substituents R$^{2\prime}$ and R$^{3\prime}$ may be partially or fully substituted by F, Cl and/or Br, or partially by NO$_2$ or CN, and
where, in the substituents R$^{1\prime}$ to R$^{4\prime}$, one or two non-adjacent carbon atoms which are not bonded directly to the heteroatom and are not in the ω-position may be replaced by —O—, —C(O)—, —S—, —S(O)— or —SO$_2$—,
where the halides are selected from the group consisting of chlorides, bromides, iodides, and uronium iodide.

11. The process according to claim 1, wherein the halide is an ammonium halide.
12. The process according to claim 8, wherein R$^1$ to R$^4$ and R$^7$ each, independently of one another, denote
hydrogen or CN, where hydrogen is excluded for R$^7$,
straight-chain or branched alkyl having 1 to 20 C atoms,
straight-chain or branched alkenyl having 2-20 C atoms and one or more double bonds, or
straight-chain or branched alkynyl having 2-20 C atoms and one or more triple bonds, saturated, partially or fully unsaturated cycloalkyl having 3-7 C atoms, which may be substituted by alkyl groups having 1-6 C atoms,
where one or more of the substituents R$^1$ to R$^4$ and R$^7$ may be partially or fully substituted by F and/or Cl, or partially by CN, but where all substituents on an N atom cannot be fully substituted by halogens,
where the substituents R$^1$ to R$^4$ and R$^7$ may be connected to one another in pairs by a single or double bond, and
where, in the substituents R$^1$ to R$^4$ and R$^7$, one or two non-adjacent carbon atoms which are not bonded directly to the heteroatom and are not in the ω-position may be replaced by —O—, —C(O)—, —S—, —S(O)— or —SO$_2$—.
13. The process according to claim 9, wherein R$^{1\prime}$ to R$^{4\prime}$ each, independently of one another, denote
hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, dialkylamino containing alkyl groups having 1-4 C atoms, which, however, is not bonded to the heteroatom of the heterocycle,
saturated, partially or fully unsaturated cycloalkyl having 3-7 C atoms, which may be substituted by alkyl groups having 1-6 C atoms, or
aryl-C$_1$-C$_6$-alkyl,
where the substituents R$^{1\prime}$ and R$^{4\prime}$ may be partially or fully substituted by F and/or Cl, but where R$^{1\prime}$ and R$^{4\prime}$ are not simultaneously CN or cannot simultaneously be fully substituted by F or other halogens,
where the substituents R$^{2\prime}$ and R$^{3\prime}$ may be partially or fully substituted by F and/or Cl, or partially by NO$_2$ or CN, and
where, in the substituents R$^{1\prime}$ to R$^{4\prime}$, one or two non-adjacent carbon atoms which are not bonded directly to the heteroatom and are not in the ω-position may be replaced by —O—, —C(O)—, —S—, —S(O)— or —SO$_2$—.
14. The process according to claim 5, wherein the reaction of the halide with the dialkyl sulfite is carried out without a solvent.

* * * * *